(12) United States Patent
Schaefer et al.

(10) Patent No.: US 7,932,386 B2
(45) Date of Patent: Apr. 26, 2011

(54) PREPARATION OF 2-AMINO-THIAZOLE-5-CARBOXYLIC-ACID DERIVATIVES

(75) Inventors: Bernd Schaefer, Dierbach (DE); Frank Haunert, Mannheim (DE); Norbert Goetz, Worms (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 474 days.

(21) Appl. No.: 12/166,410

(22) Filed: Jul. 2, 2008

(65) Prior Publication Data

US 2009/0030203 A1    Jan. 29, 2009

Related U.S. Application Data

(62) Division of application No. 11/498,650, filed on Aug. 3, 2006, now Pat. No. 7,408,069.

(30) Foreign Application Priority Data

Aug. 5, 2005 (EP) ..................................... 05107247
Aug. 11, 2005 (EP) ..................................... 05107375

(51) Int. Cl.
*C07D 417/14* (2006.01)
(52) U.S. Cl. .................. 544/295; 544/224; 544/242
(58) Field of Classification Search .................. 544/224, 544/242, 295
See application file for complete search history.

(56) References Cited

U.S. PATENT DOCUMENTS

| | | |
|---|---|---|
| 6,596,746 B1 | 7/2003 | Das et al. |
| 7,091,223 B2 * | 8/2006 | Das et al. ........................ 514/342 |
| 7,408,069 B2 * | 8/2008 | Schaefer et al. ............... 548/195 |
| 7,491,725 B2 * | 2/2009 | Lajeunesse et al. ...... 514/252.19 |
| 2005/0215795 A1 | 9/2005 | Chen et al. |
| 2005/0261305 A1 | 11/2005 | Das et al. |

FOREIGN PATENT DOCUMENTS

| | | |
|---|---|---|
| DE | 2436653 | 2/1975 |
| EP | 275312 | 7/1988 |
| WO | WO03/082838 | 10/2003 |
| WO | WO2004/002948 | 8/2004 |
| WO | WO2004/081001 | 9/2004 |
| WO | WO2005/077945 | 8/2005 |

OTHER PUBLICATIONS

Zhao et al., "A new facile synthesis of 2-aminothiazole-5-carboxylates", Tetrahedron Letters, 2001, vol. 42, No. 11, pp. 2101-2102.

Wityak et al., "Discovery and initial SAR of 2-amino-5-carboxamiclothiazoles as inhibitors of the Src-family kinase p56Lck", Bioorganic and Medicinal Chemistry Letters, 2003, vol. 13, No. 22, pp. 4007-4010.

* cited by examiner

*Primary Examiner* — Golam M Shameem
(74) *Attorney, Agent, or Firm* — Mary K. Van Atten

(57) ABSTRACT

A method for preparing a compound of the structure I,

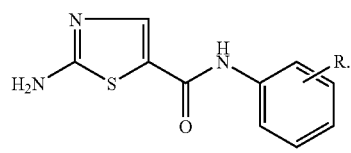

4 Claims, No Drawings

PREPARATION OF 2-AMINO-THIAZOLE-5-CARBOXYLIC-ACID DERIVATIVES

CROSS-REFERENCE TO RELATED APPLICATIONS

This application is a divisional application of U.S. application Ser. No. 11/498,650 filed Aug. 3, 2006 which claims the benefit of priority under 35 U.S.C. § 119(b) to European Patent Application No. 05107247.8 filed Aug. 5, 2005 and European Patent Application No. 05107375.7 filed Aug. 11, 2005, the contents of which are herein incorporated by reference.

The present invention relates to a novel synthetic route to 2-amino-thiazole-5-carboxylic-acid-aryl amides of the formula I.

Aryl-substituted 2-Amino-5-thiazole-carboxamides of the type of the Compounds of Formula I are known from U.S. Pat. No. 6,596,746 as intermediates in the synthesis of pharmaceutical active ingredients. The compounds are obtained by reaction of an amine-protected thiazole carboxylic acid chloride with a substituted aniline in the presence of a base followed by removal of the amine protective group.

According to EP-A 275 312 substituted amino thiazoles can be obtained by reaction of substituted thiourea with an α-chloro carbonyl compound wherein the carbonyl compound may be protected as a dialkyl acetal.

According to US Statutory Invention Registration No. H1737 compounds of the type of Formula II are disclosed as intermediates in the synthesis of pharmaceutical active ingredients.

The reaction of dichloroacrylic acid chloride with amines such as 6-Chloro-2-methyl-aniline is disclosed in DE-A 2436653.

The object of the present invention was to find an improved method for making compounds of the Formula I.

The present invention provides for an improved method for preparing a compound of the structure I,

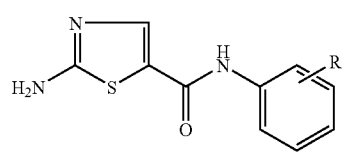

wherein R is aryl, substituted with one or more residues selected from the group consisting of chlorine, methyl, ethyl, methoxy and ethoxy, which comprises providing a compound of the structure II

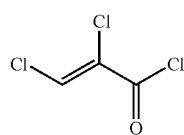

and reacting the above compound with substituted anilines of the structure III,

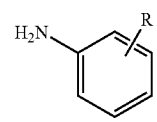

wherein R has the same meaning as above, in the presence of an inorganic base and subjecting the reaction mixture to a reaction with an alkanolate salt to give a compound of formula IV,

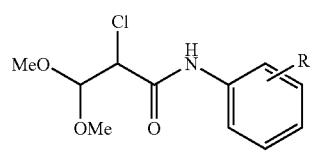

which compound is reacted with thiourea in an acidic medium to give the compound of formula I.

The present invention also provides for novel intermediates of formula IV.

The starting compound dichloro acrylic acid chloride II can be obtained in any known manner, for instance by alkaline hydrolysis of mucochloric acid to 2,3-dichloro acrylic acid and further reaction to the acid chloride (Compound II).

The overall synthetic route can be carried out as outlined in the following simplified scheme A:

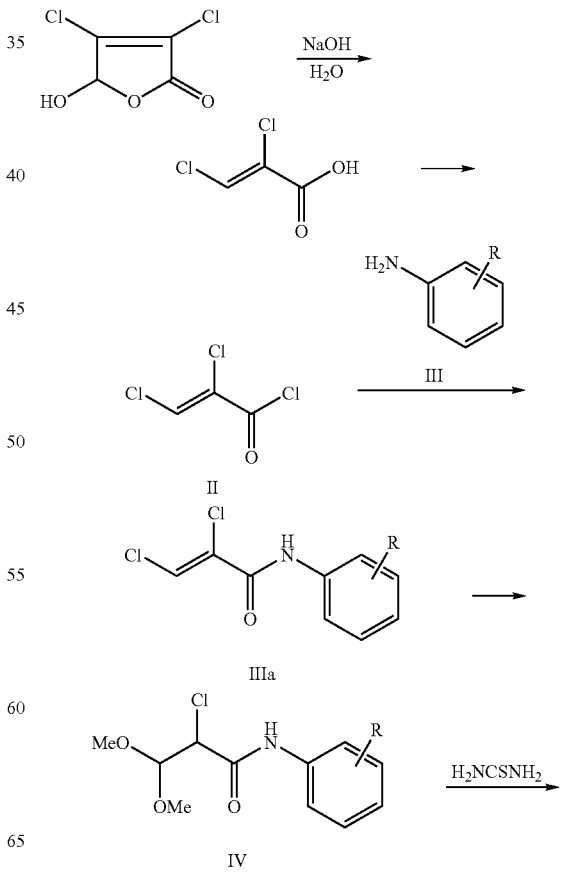

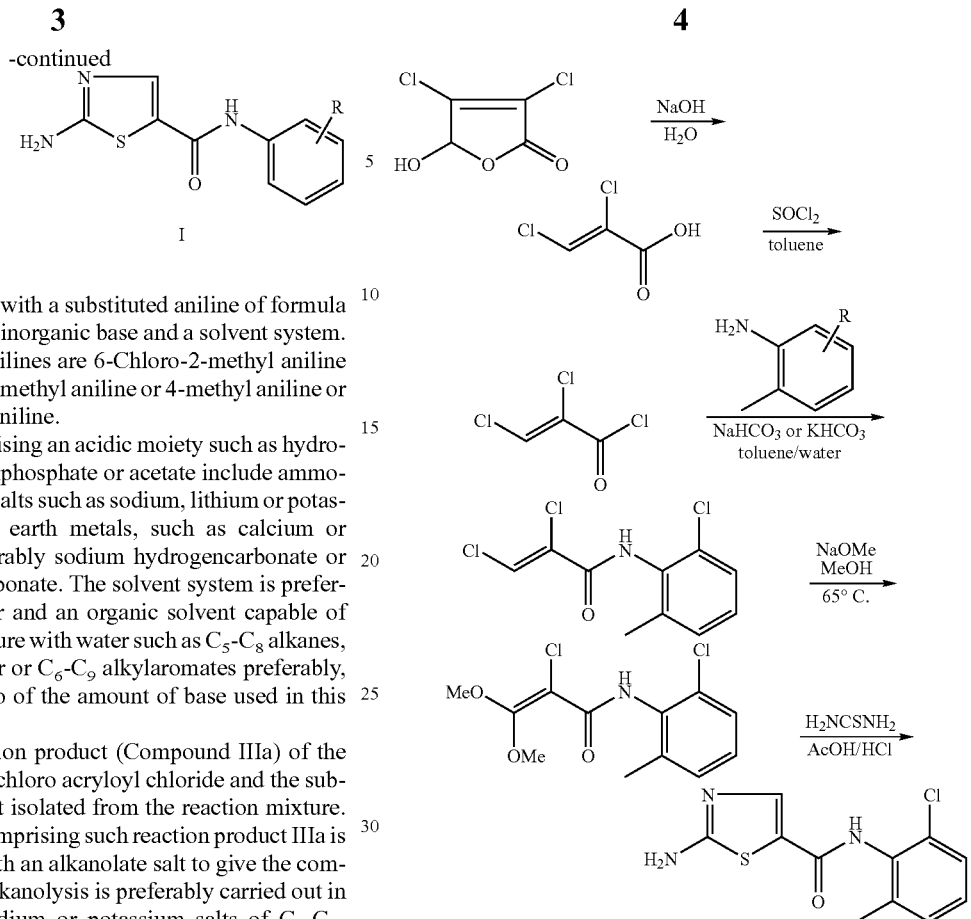

Compound II is reacted with a substituted aniline of formula III in the presence of an inorganic base and a solvent system. Preferred substituted anilines are 6-Chloro-2-methyl aniline or 2-methyl aniline or 3-methyl aniline or 4-methyl aniline or 4,6-dichloro-2-methyl aniline.

Suitable bases comprising an acidic moiety such as hydrogencarbonate, hydrogenphosphate or acetate include ammonium salts, alkali metal salts such as sodium, lithium or potassium salts, or alkaline earth metals, such as calcium or magnesium salts, preferably sodium hydrogencarbonate or potassium hydrogencarbonate. The solvent system is preferably a mixture of water and an organic solvent capable of forming a biphasic mixture with water such as $C_5$-$C_8$ alkanes, $C_4$-$C_8$ ether, $C_4$-$C_8$ ester or $C_6$-$C_9$ alkylaromates preferably, toluene. The molar ratio of the amount of base used in this reaction is 1 to 10.

The immediate reaction product (Compound IIIa) of the reaction between 2,3-dichloro acryloyl chloride and the substituted aniline III is not isolated from the reaction mixture. The reaction mixture comprising such reaction product IIIa is subsequently treated with an alkanolate salt to give the compound of formula IV. Alkanolysis is preferably carried out in the presence of the sodium or potassium salts of $C_1$-$C_6$-alkanols or $C_2$-$C_7$-alkanediols, sodium methanolate being the most preferred alkanolate salt. The respective alkanol is preferably used as solvent for the reaction. The molar ratio of the amount of alkanolate salt used in this reaction is 1-5.

The compound of formula IV is reacted with thiourea in an acidic medium to give the target compound I. The acidic medium is provided by the presence of a strong acid. Suitable strong acids are hydrochloric acid or hydrobromic acid, preferably hydrochloric acid. The reaction can be carried out in a solvent such as formic acid, acetic acid, propionic acid or trifluoro acetic acid.

In a preferred method the reaction is carried out in a mixture of HCl as an acid and acetic acid as the solvent. The molar ratio of acid to compound IV is 1-10.

The resulting thiazole derivative is obtained as the salt of the strong acid, from which the free base can be obtained by any known manner, for instance by treating the salt with a base. The preferred base is sodium methanolate.

Purification of the target compound can be carried by recrystallization.

Preferably, purification is carried out by recrystallization in solvents such as $C_5$-$C_8$ alkanes, $C_4$-$C_8$ ether, $C_4$-$C_8$ ester, $C_1$-$C_6$ alcohols or $C_6$-$C_9$ alkylaromates and water, preferably THF, hexane, methanol and water or mixtures thereof. Preferably the recrystallization is carried out at temperatures from −20 to 100° C., especially 0 and 60° C.

All steps of the synthesis are carried out under reflux of the respective solvent used in each step at 40 to 70° C., preferably at 50 to 65° C. The reaction can be carried out at atmospheric pressure.

Preferably the invention provides for an improved method as outlined in the following scheme B:

According to the inventive method the target molecule can be produced in high yields and high purities.

Additionally, the compounds of Formula I may be useful in the preparation of the compound of formula V, see the following Scheme C:

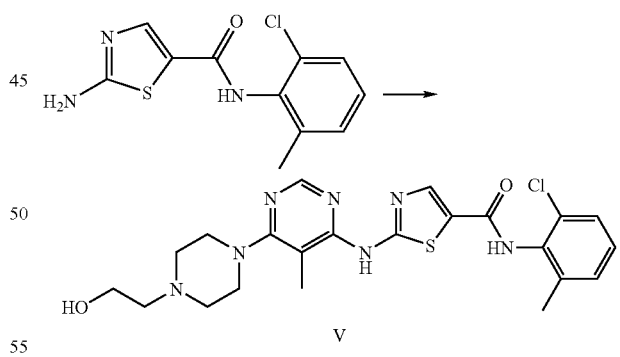

The compound of Formula V may be prepared as described in WO00/62778, and in WO2005/077945, which are hereby incorporated by reference.

EXAMPLE 1

Preparation of 2,3-dichloro acrylic acid

A 4000 l vessel was charged with 1800 l of demineralized water and 460 kg of caustic soda (50 wt. % aqueous solution) and heated to 40° C. while stirring. Within 2 hours 400 kg of mucochloric acid were added to the reaction mixture with the temperature of the reaction mixture varying from 10 to 50° C. After the addition had been completed the reaction mixture was stirred for 1 hour at 40° C. The vessel was cooled to 25° C. and 600 l hydrochloric acid (37% b.w., aqueous) were added. Afterwards the reaction mixture was cooled to 0° C. and stirred at that temperature for one hour. The resulting suspension was filtered by a centrifuge. Yield: 67%.

EXAMPLE 2

Preparation of a 2,3-dichloro acrylic chloride

A 2000 l reaction vessel was charged with 165 kg muco chloric acid, 400 kg toluene and 0.85 kg DMF. Then 420 kg thionylchloride is added at 70° C. within 4 h. After gas evolution has ceased thionylchloride and toluene were distilled off at reduced pressure. Afterwards the product was distilled at 95° C./50 mbar. Yield: 87%.

EXAMPLE 3

Preparation of a 2-chloro-N-(2-chloro-6-methyl-phenyl)-3,3-dimethoxy-propionamide A 4000 l vessel was charged with 187 kg of potassium hydrogencarbonate and 561 l of water under a nitrogen atmosphere. After the mixture had been stirred at ambient temperature for half an hour 156 kg of 2-chloro-6-methyl-aniline and 193 l of toluene were added and the mixture heated to 60-65° C. Then 280 kg of a 75% b.w. solution of 2,3 dichloro acryloyl chloride in toluene were added within four hours and the reaction mixture was stirred for additional two hours. Then 440 l toluene were charged into the vessel and the phases were separated. During addition of the dichloro acryloyl chloride solution, additional stirring and phase separation the temperature was kept at 60-65° C. The organic phase was subjected to vacuum distillation and water and toluene were distilled off. 1375 l of methanol were charged into the vessel and distillation was continued until the residual toluene was removed. Then 198 kg of a 30% b.w. solution of sodium methanolate in methanol were added at 50° C. within two hours and the resulting mixture stirred for another five hours at 50° C. The mixture was cooled to 20-25° C. and 110 l of methanol were distilled off at 500 mbar.

EXAMPLE 4

Preparation of 2-Amino-thiazole-5-carboxylic acid (2-chloro-6-methyl-phenyl)-amide The vessel with the product obtained according to Example 2 was purged with nitrogen and the reaction mixture diluted with 1023 l of acetic acid. Residual methanol was distilled off as a mixture with acetic acid. After 253 l of acetic acid and 109 kg of hydrochloric acid (37% b.w. of HCl) had been added at 50° C. 92 kg of thiourea were charged into the vessel and the reaction mixture heated to 60-65° C. and stirred for eleven hours. About 715 l of acetic acid were distilled off at 100 mbar and 847 l of methanol were added. After about 780 l of a methanol/acetic acid mixture had been distilled off at atmospheric pressure 847 l of methanol and 135 kg of a 30% b.w. solution of sodium methanolate in methanol were added in portions to adjust the pH at pH 8-9. The precipitated salts were filtered off and the filtrate was treated with 125 kg charcoal at 60° C. for several hours. After removal of the charcoal by filtration 1000 l methanol are distilled off at 500 mbar. Then 2000 l water are added and the reaction mixture in cooled down to 0° C. The product is filtered off. The filter cake was dried by purging it with nitrogen at 50° C.

In a 4000 l vessel 130 kg of the crude thiazol are dissolved in 870 kg THF at 50° C. and 640 kg hexane are added at 20° C. within 3 h. the suspension is cooled down to 0° C. and the product is filtered off. the filter cake is washed with 380 l hexane and dried in a drying chamber. Overall Yield: 68%.

We claim:
1. A method for preparing a compound of the structure V

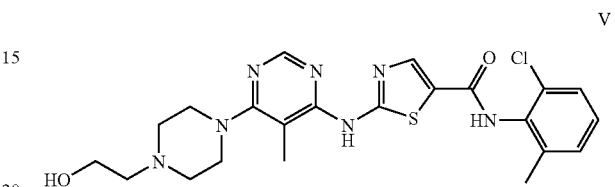

which comprises providing a compound of the structure II

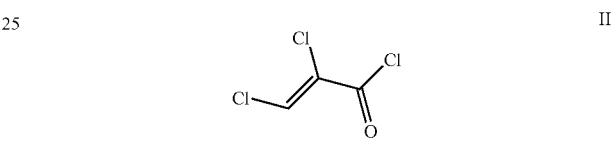

and reacting the above compound with substituted anilines of the structure III,

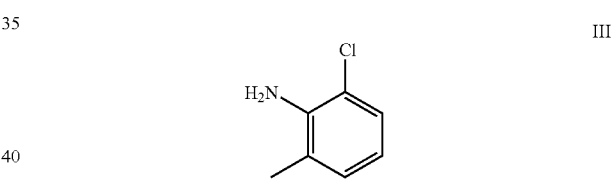

in the presence of an inorganic base and subjecting the reaction mixture to a reaction with an alkanolate salt to give a compound of formula IV,

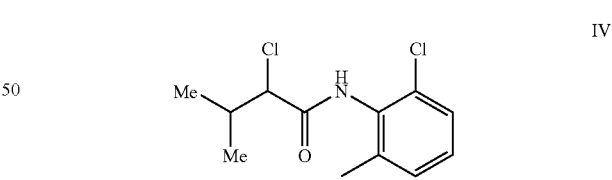

which compound is reacted with thiourea in an acidic medium to give the compound of formula I,

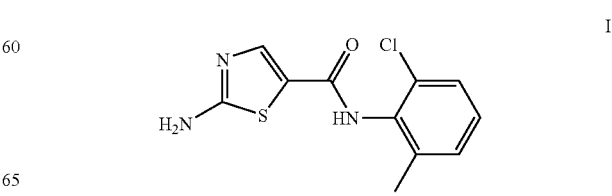

the compound of formula I is reacted with 4,6-dichloro-2-methyl-pyrimidine, followed by 2-piperazin-1-yl-ethanol to give the compound of formula V.

2. A method as defined in claim 1, wherein the base is sodium hydrogencarbonate or potassium hydrogencarbonate.

3. A method as defined in any of claim 2, wherein the alkanolate salt is sodium methanolate.

4. A method as defined in any of claim 3, wherein the starting compound II is prepared by alkaline hydrolysis of mucochloric acid and subsequent formation of the acyl chloride of 2,3-dichloro acrylic acid.

* * * * *